United States Patent
Georges et al.

(10) Patent No.: US 7,956,190 B2
(45) Date of Patent: Jun. 7, 2011

(54) BENZIMIDAZOLE AMIDO DERIVATIVES AS KINASE INHIBITORS

(75) Inventors: Guy Georges, Habach (DE); Eike Hoffmann, Seefeld (DE); Klaus Kaluza, Bad Heilbrunn (DE); Matthias Koerner, Grenzach-Wyhlen (DE); Ulrike Reiff, Penzberg (DE); Stefan Weigand, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/600,662

(22) PCT Filed: Jun. 23, 2008

(86) PCT No.: PCT/EP2008/005055
§ 371 (c)(1),
(2), (4) Date: Nov. 18, 2009

(87) PCT Pub. No.: WO2009/000489
PCT Pub. Date: Dec. 31, 2008

(65) Prior Publication Data
US 2010/0168181 A1    Jul. 1, 2010

(30) Foreign Application Priority Data
Jun. 25, 2007 (EP) .................................. 07012354

(51) Int. Cl.
*C07D 401/00* (2006.01)
(52) U.S. Cl. .................................................. 546/273.4
(58) Field of Classification Search .......... None
See application file for complete search history.

(56) References Cited

FOREIGN PATENT DOCUMENTS

| | | |
|---|---|---|
| WO | WO 00/44728 | 8/2000 |
| WO | WO 02/22601 | 3/2002 |
| WO | WO 02/079192 | 10/2002 |
| WO | WO 2004/018419 | 3/2004 |
| WO | WO 2004/031401 | 4/2004 |
| WO | WO 2004/063151 | 7/2004 |
| WO | WO 2005/002576 | 1/2005 |
| WO | WO 2005/021510 | 3/2005 |
| WO | WO 2005/046589 | 5/2005 |
| WO | WO 2007/056155 | 5/2007 |

*Primary Examiner* — Janet L Andres
*Assistant Examiner* — Heidi Reese
(74) *Attorney, Agent, or Firm* — George W. Johnston; Patricia S. Rocha-Tramaloni; David E. Wildman

(57) ABSTRACT

Objects of the present invention are the compounds of formula (I) their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

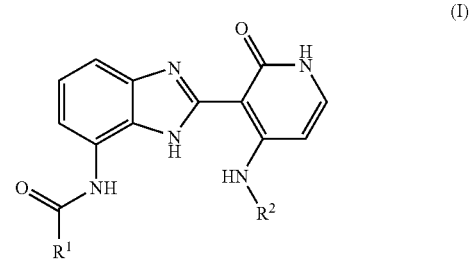

10 Claims, No Drawings

BENZIMIDAZOLE AMIDO DERIVATIVES AS KINASE INHIBITORS

This application is the national stage of International Application No. PCT/EP2008/005055, filed Jun. 23, 2008, which claims the benefit of European Application No. 07012354.2, filed Jun. 25, 2007, which is hereby incorporated by reference in its entirety.

The present invention relates to novel benzimidazole amido derivatives, to a process for their manufacture, pharmaceutical compositions containing them and their manufacture as well as the use of these compounds as pharmaceutically active agents.

BACKGROUND OF THE INVENTION

Protein kinases ("PKs") are enzymes that catalyze the phosphorylation of hydroxy groups on tyrosine, serine and threonine residues of proteins (Hunter, T., Cell 50 (1987) 823-829). The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, Neuron, 9 (1992) 303-391, which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epidermal growth factor receptor), HER2 (human epidermal growth factor receptor 2), HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily is referred to as the platelet derived growth factor receptor ("PDGFR") group, which includes PDGFR alpha, PDGFR beta, colony-stimulating factor 1 receptor (CSF-1R), c-kit and flt-3. These receptors consist of glycosylated extracellular domains composed of 5 immunoglobin-like loops and an intracellular domain wherein the tyrosine kinase domain is interrupted by a kinase inert domain.

Another group which, because of its similarity to the PDGFR subfamily, is sometimes subsumed into the latter group is the fetal liver kinase ("Flk") receptor subfamily. This group, containing extracellular immunoglobulin loops made up of kinase insert domain receptor/fetal liver kinase-1 (KDR/Flk-1), and fms-like tyrosine kinase 1 (Flt-1 and Flt-4). The human analogue of FLK-1 is the kinase insert domain-containing receptor KDR, which is also known as vascular endothelial cell growth factor receptor 2 or VEGFR-2, since it binds VEGF with high affinity.

Of the three PTK (protein tyrosine kinases) receptors for VEGFR identified VEGFR-1 (Flt-1); VEGRF-2 (Flk-1 or KDR) and VEGFR-3 (Flt-4), VEGFR-2 is of peculiar interest.

The Aurora kinases are a family of serine/threonine kinases that are believed to play a key role in the protein phosphorylation events that are essential for the completion of essential mitotic events. The Aurora kinase family is made up of three key members: Aurora A, B and C (also known as Aurora-2, Aurora-1 and Aurora-3, respectively). Aurora-1 and Aurora-2 are described in U.S. Pat. No. 6,207,401 of Sugen and in related patents and patent applications, e.g. EP 0 868 519 and EP 1 051 500.

For Aurora A there is increasing evidence that it is a novel proto-oncogene. Aurora A gene is amplified and transcript/protein is highly expressed in a majority of human tumor cell lines and primary colorectal, breast and other tumors. It has been shown that Aurora A overexpression leads to genetic instability shown by amplified centrosomes and significant increase in aneuploidy and transforms Rat1 fibroblasts and mouse NIH3T3 cells in vitro. Aurora A-transformed NIH3T3 cells grow as tumors in nude mice (Bischoff, J. R., and Plowman, G. D., Trends Cell Biol. 9 (1999) 454-459; Giet, R., and Prigent, C., J. Cell Sci. 112 (1999) 3591-3601; Nigg, E. A., Nat. Rev. Mol. Cell. Biol. 2 (2001) 21-32; Adams, R. R., et al., Trends Cell Biol. 11 (2001) 49-54). Moreover, amplification of Aurora A is associated with aneuploidy and aggressive clinical behavior (Sen, S., et al., J. Natl. Cancer Inst. 94 (2002) 1320-1329) and amplification of its locus correlates with poor prognosis for patients with node-negative breast cancer (Isola, J., J., et al., Am. J. Pathology 147 (1995) 905-911). For these reasons it is proposed that Aurora A overexpression contributes to cancer phenotype by being involved in chromosome segregation and mitotic checkpoint control.

Human tumor cell lines depleted of Aurora A transcripts arrest in mitosis. Accordingly, the specific inhibition of Aurora kinase by selective inhibitors is recognized to stop uncontrolled proliferation, re-establish mitotic checkpoint control and lead to apoptosis of tumor cells. In a xenograft model, an Aurora inhibitor therefore slows tumor growth and induces regression (Harrington, E., A., et al., Nat. Med. 10 (2004) 262-267).

Low molecular weight inhibitors for protein kinases are widely known in the state of the art. For Aurora inhibition such inhibitors are based on i.e. pyrazole or quinazoline derivatives as claimed in the following patents and patent applications: WO 00/44728 or WO 02/22601.

WO 02/079192, WO 2004/031401, WO 2004/018419, WO 2004/063151 and WO 2005/021510 relate to benzimidazole pyridone derived kinase inhibitors. WO 2007/056155 relates to heterocyclic compounds as tyrosine kinase modulators. WO 2005/046589 describes benzimidazole quinolinones and lactate salts thereof for inhibiting vascular endothelial growth factor receptor tyrosine kinase.

SUMMARY OF THE INVENTION

The present invention relates to indole derivatives of the general formula I,

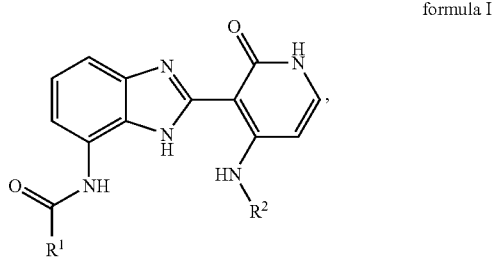

formula I wherein
R$^1$ is —R$^3$, —O—R$^3$ or —NR—R$^3$;
R$^2$ is —X—R$^4$;
R$^3$ is a) —(CH$_2$)$_n$—(O)$_m$-phenyl, wherein the phenyl is unsubstituted or substituted one to three times independently by alkyl, —O-alkyl, halogen, cyano, —N(alkyl)$_2$, trifluoromethyl, trifluoromethoxy; with the proviso that if R$^1$ is —O—R$^3$, or —NR—R$^3$, and n is 0, m is also 0.
  b) alkyl, wherein the alkyl is unsubstituted or substituted one to three times independently by —O-alkyl or halogen;
  c) alkenyl;
  d) heteroaryl; or
  e) (C$_3$-C$_6$) cycloalkyl;
R$^4$ is a) phenyl, wherein the phenyl is unsubstituted or substituted one to three times by halogen, alkyl, —O-alkyl, —N(alkyl)$_2$, trifluoromethyl or trifluoromethoxy; or
  b) pyridyl.
X is (C$_1$-C$_3$)alkylene, wherein the alkylene is unsubstituted or substituted once or twice by hydroxy, alkyl or halogen;
R is hydrogen or (C$_1$-C$_3$)alkyl;
m is 0 or 1;
n is 0, 1 or 2;
and all pharmaceutically acceptable salts thereof.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as kinase inhibitors, especially as Aurora kinase inhibitors.

Objects of the present invention are the compounds of formula I and their tautomers, pharmaceutically acceptable salts, enantiomeric forms, diastereoisomers and racemates, their use as protein kinase inhibitors, in particular as Aurora kinase inhibitors, the preparation of the above-mentioned compounds, medicaments or pharmaceutical compositions containing them and their manufacture as well as the use of the above-mentioned compounds in treatment, control or prevention of illnesses, especially of illnesses and disorders as mentioned above like tumors or cancer (e.g. colorectal, breast, lung, prostate, pancreatic, gastric, bladder, ovarian, melanoma, neuroblastoma, cervical, kidney or renal cancers, leukemias or lymphomas) or in the manufacture of corresponding medicaments or pharmaceutical compositions.

DETAILED DESCRIPTION OF THE INVENTION

1. Definitions

The term "alkyl" as used herein means a saturated, straight-chain or branched-chain hydrocarbon containing from 1 to 6 carbon atoms, preferably from 1 to 4 carbon atoms, such as methyl, ethyl, n-propyl, isopropyl, n-butyl, 2-butyl, t-butyl, n-pentyl, n-hexyl. The term "(C$_1$-C$_3$)alkyl" as used herein means an alkyl as defined above containing from 1 to 3 carbon atoms.

The term "halogen" as used herein means fluorine, chlorine or bromine, preferably fluorine or chlorine and more preferably chlorine.

The term "(C$_1$-C$_3$)alkylene" as used herein means a saturated, straight-chain or branched-chain, preferably straight-chain, hydrocarbon containing from 1 to 3 carbon atoms, such as methylene, ethylene, trimethylene (1,3-propylene); methyl-methylene, ethyl-methylene, methyl-ethylene (1,2-propylene), preferably methylene or ethylene.

The term "—O-alkyl" as used herein means an alkyl group as defined with is attached via an oxygen atom, such as methoxy, ethoxy, n-propoxy or isopropoxy and the like, preferably methoxy.

The term "alkenyl" as used herein means an unsaturated straight-chain or branched aliphatic hydrocarbon group containing one double bond and having 2 to 4, preferably 2 to 3 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, preferably allyl.

The term "heteroaryl" as used herein means a mono- or bicyclic aromatic ring with 5 to 6 ring atoms, which contains up to 3 heteroatoms, preferably 1 or 2 heteroatoms, selected independently from N, O or S and the remaining ring atoms being carbon atoms. Examples of such heteroaryl groups include pyrrolyl, imidazolyl, pyrazolyl, triazolyl, tetrazolyl, furanyl, oxazolyl, isoxazolyl, thienyl, thiazolyl, pyridyl, pyrimidyl, pyridazinyl, pyrazinyl, and the like, preferably furanyl.

The term "(C$_3$-C$_6$) cycloalkyl" means a monocyclic saturated hydrocarbon ring with 3 to 6, ring atoms. Examples of such saturated carbocyclic groups are cyclopropyl, cyclobutyl, cyclopentyl and cyclohexyl, preferably cyclopropyl.

2. Detailed Description

R$^1$ is —R$^3$, —O—R$^3$ or —NR—R$^3$; preferably —R$^3$ or —NR—R$^3$.
R$^2$ is —X—R$^4$.
R$^3$ is a) —(CH$_2$)$_n$—(O)$_m$-phenyl, wherein the phenyl is unsubstituted or substituted one to three times independently by alkyl, —O-alkyl, halogen, cyano, —N(alkyl)$_2$, trifluoromethyl, trifluoromethoxy; preferably one or two times by —O—CH$_3$, cyano, fluorine, chlorine, trifluoromethyl or trifluoromethoxy; with the proviso that if R$^1$ is —O—R$^3$, or —NR—R$^3$, and n is 0, m is also 0;
b) alkyl, wherein the alkyl is unsubstituted or substituted one to three times, independently by —O-alkyl or halogen; preferably by —O—CH$_3$ or chlorine;
c) alkenyl; preferably allyl;
d) heteroaryl; preferably furanyl; or
e) (C$_3$-C$_6$) cycloalkyl; preferably cyclopropyl.

R⁴ is a) phenyl, wherein the phenyl is unsubstituted or substituted one to three times by halogen, alkyl, —O-alkyl, —N(alkyl)₂ trifluoromethyl or trifluoromethoxy; preferably once by chlorine; or
b) pyridyl.
X is (C₁-C₃)alkylene, wherein the alkylene is unsubstituted or substituted once or twice by hydroxy, alkyl or halogen; preferably once by hydroxy.
R is hydrogen or (C₁-C₃)alkyl; preferably hydrogen.
m is 0 or 1; preferably 0.
n is 0, 1 or 2; preferably 0 or 1.
An embodiment of the invention are the compounds according to formula I, characterized in that
  R³ is a) —(CH₂)ₙ—(O)ₘ-phenyl, wherein the phenyl is unsubstituted or substituted one or two times independently by —O—CH₃, cyano, fluorine, chlorine, trifluoromethyl or trifluoromethoxy; with the proviso that if R¹ is —O—R³, or —NR—R³, and n is 0, m is also 0.
    b) alkyl, wherein the alkyl is unsubstituted or substituted one to three times independently by —O—CH₃ or chlorine;
    c) allyl;
    d) furanyl;
    e) cyclopropyl;
  R⁴ is a) phenyl, wherein the phenyl is unsubstituted or substituted once by chlorine; or
    b) pyridyl;
  X is (C₁-C₃)alkylene, wherein the alkylene is unsubstituted or substituted once by hydroxy; and
  R is hydrogen; and
  n is 0 or 1.
Another embodiment of the invention are the compounds according to formula I, characterized in that
  R¹ is —R³ or —NR—R³;
  R³ is a) —(CH₂)ₙ—(O)ₘ-phenyl, wherein the phenyl is unsubstituted or substituted one or two times independently by —O—CH₃, cyano, chlorine, trifluoromethyl or trifluoromethoxy; with the proviso that if R¹ is —O—R³, or —NR—R³, and n is 0, m is also 0.
    b) alkyl, wherein the alkyl is substituted once by —O—CH₃;
    c) furanyl;
    d) cyclopropyl;
  R⁴ is a) phenyl, wherein the phenyl is unsubstituted or substituted once by chlorine; or
    b) pyridyl;
  X is (C₁-C₃)alkylene, wherein the alkylene is unsubstituted or substituted once by hydroxy; and
  R is hydrogen; and
  n is 0 or 1.
Another embodiment of the invention are the compounds according to formula I, characterized in that
  R¹ is —R³.
Another embodiment of the invention are the compounds according to formula I, characterized in that
  R¹ is —R³; and
  R³ is a) —(CH₂)ₙ—(O)ₘ-phenyl, wherein the phenyl is unsubstituted or substituted one or two times independently by —O—CH₃, cyano, fluorine, chlorine, trifluoromethyl or trifluoromethoxy; with the proviso that if R¹ is —O—R³, or —NR—R³, and n is 0, m is also 0.
    b) alkyl, wherein the alkyl is substituted once by —O—CH₃;
    c) furanyl; or
    d) cyclopropyl.

Such compounds, for example, may be selected from the group consisting of
3-Cyano-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
N-[2-(4-Benzylamino-2-oxo-1,2-dihydro-pyridin-3-yl)-3H-benzoimidazol-4-yl]-2,4-difluoro-benzamide; compound with hydrochloric acid;
N-[2-(4-Benzylamino-2-oxo-1,2-dihydro-pyridin-3-yl)-3H-benzoimidazol-4-yl]-4-methoxy-benzamide; compound with hydrochloric acid;
N-[2-(4-Benzylamino-2-oxo-1,2-dihydro-pyridin-3-yl)-3H-benzoimidazol-4-yl]-benzamide; compound with hydrochloric acid;
N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
4-Methoxy-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
4-Chloro-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
N-{2-[4-(3-Chloro-benzylamino)-2-oxo-1,2-dihydro-pyridin-3-yl]-3H-benzoimidazol-4-yl}-4-methoxy-benzamide; compound with hydrochloric acid;
4-Chloro-N-{2-[4-(3-chloro-benzylamino)-2-oxo-1,2-dihydro-pyridin-3-yl]-3H-benzoimidazol-4-yl}-benzamide; compound with hydrochloric acid;
N-{2-[4-(3-Chloro-benzylamino)-2-oxo-1,2-dihydro-pyridin-3-yl]-3H-benzoimidazol-4-yl}-2,4-difluoro-benzamide; compound with hydrochloric acid;
3-Chloro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;
4-Fluoro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;
3,4-Dichloro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;
N-{2-[4-((S)-2-Hydroxy-2-phenyl-ethylamino)-2-oxo-1,2-dihydro-pyridin-3-yl]-3H-benzoimidazol-4-yl}-3-phenyl-propionamide; compound with hydrochloric acid;
N-{2-[4-((S)-2-Hydroxy-2-phenyl-ethylamino)-2-oxo-1,2-dihydro-pyridin-3-yl]-3H-benzoimidazol-4-yl}-4-trifluoromethyl-benzamide; compound with hydrochloric acid;
N-[2-(4-Benzylamino-2-oxo-1,2-dihydro-pyridin-3-yl)-3H-benzoimidazol-4-yl]-2-methoxy-benzamide; compound with hydrochloric acid;
N-[2-(4-Benzylamino-2-oxo-1,2-dihydro-pyridin-3-yl)-3H-benzoimidazol-4-yl]-2-chloro-benzamide; compound with hydrochloric acid;
N-[2-(4-Benzylamino-2-oxo-1,2-dihydro-pyridin-3-yl)-3H-benzoimidazol-4-yl]-4-chloro-benzamide; compound with hydrochloric acid;
N-{2-[4-((S)-2-Hydroxy-2-phenyl-ethylamino)-2-oxo-1,2-dihydro-pyridin-3-yl]-3H-benzoimidazol-4-yl}-2-phenyl-acetamide;
N-{2-[4-(3-Chloro-benzylamino)-2-oxo-1,2-dihydro-pyridin-3-yl]-3H-benzoimidazol-4-yl}-benzamide;
N-{2-[4-((S)-2-Hydroxy-2-phenyl-ethylamino)-2-oxo-1,2-dihydro-pyridin-3-yl]-3H-benzoimidazol-4-yl}-2,2-dimethyl-propionamide;
N-{2-[4-((S)-2-Hydroxy-2-phenyl-ethylamino)-2-oxo-1,2-dihydro-pyridin-3-yl]-3H-benzoimidazol-4-yl}-4-methoxy-benzamide;

N-{2-[4-((S)-2-Hydroxy-2-phenyl-ethylamino)-2-oxo-1,2-dihydro-pyridin-3-yl]-3H-benzoimidazol-4-yl}-3-trifluoromethyl-benzamide;

N-{2-[4-((S)-2-Hydroxy-2-phenyl-ethylamino)-2-oxo-1,2-dihydro-pyridin-3-yl]-3H-benzoimidazol-4-yl}-2-phenoxy-acetamide;

N-{2-[4-((S)-2-Hydroxy-2-phenyl-ethylamino)-2-oxo-1,2-dihydro-pyridin-3-yl]-3H-benzoimidazol-4-yl}-3,3-dimethyl-butyramide;

Cyclopropanecarboxylic acid {2-[4-((S)-2-hydroxy-2-phenyl-ethylamino)-2-oxo-1,2-dihydro-pyridin-3-yl]-3H-benzoimidazol-4-yl}-amide;

2-Fluoro-N-{2-[4-((S)-2-hydroxy-2-phenyl-ethylamino)-2-oxo-1,2-dihydro-pyridin-3-yl]-3H-benzoimidazol-4-yl}-benzamide;

2-Chloro-N-{2-[4-((S)-2-hydroxy-2-phenyl-ethylamino)-2-oxo-1,2-dihydro-pyridin-3-yl]-3H-benzoimidazol-4-yl}-benzamide;

2-(4-Chloro-phenoxy)-N-{2-[4-((S)-2-hydroxy-2-phenyl-ethylamino)-2-oxo-1,2-dihydro-pyridin-3-yl]-3H-benzoimidazol-4-yl}-acetamide;

3-Cyano-N-{2-[4-((S)-2-hydroxy-2-phenyl-ethylamino)-2-oxo-1,2-dihydro-pyridin-3-yl]-3H-benzoimidazol-4-yl}-benzamide;

N-{2-[4-((S)-2-Hydroxy-2-phenyl-ethylamino)-2-oxo-1,2-dihydro-pyridin-3-yl]-3H-benzoimidazol-4-yl}-2-methoxy-acetamide;

2,4-Difluoro-N-{2-[4-((S)-2-hydroxy-2-phenyl-ethylamino)-2-oxo-1,2-dihydro-pyridin-3-yl]-3H-benzoimidazol-4-yl]-benzamide;

3-Fluoro-N-{2-[4-((S)-2-hydroxy-2-phenyl-ethylamino)-2-oxo-1,2-dihydro-pyridin-3-yl]-3H-benzoimidazol-4-yl]-benzamide;

2,4-Dichloro-N-{2-[4-((S)-2-hydroxy-2-phenyl-ethylamino)-2-oxo-1,2-dihydro-pyridin-3-yl]-3H-benzoimidazol-4-yl}-benzamide;

N-{2-[4-((S)-2-Hydroxy-2-phenyl-ethylamino)-2-oxo-1,2-dihydro-pyridin-3-yl]-3H-benzoimidazol-4-yl}-3-methoxy-benzamide;

4-Cyano-N-{2-[4-((S)-2-hydroxy-2-phenyl-ethylamino)-2-oxo-1,2-dihydro-pyridin-3-yl]-3H-benzoimidazol-4-yl}-benzamide; and Furan-2-carboxylic acid {2-[4-((S)-2-hydroxy-2-phenyl-ethylamino)-2-oxo-1,2-dihydro-pyridin-3-yl]-3H-benzoimidazol-4-yl}-amide.

Another embodiment of the invention are the compounds according to formula I, characterized in that
$R^1$ is —O—$R^3$.

Such compounds, for example, may be selected from the group consisting of:

{2-[4-((S)-2-Hydroxy-2-phenyl-ethylamino)-2-oxo-1,2-dihydro-pyridin-3-yl]-3H-benzoimidazol-4-yl}-carbamic acid 4-methoxy-phenyl ester;

{2-[4-((S)-2-Hydroxy-2-phenyl-ethylamino)-2-oxo-1,2-dihydro-pyridin-3-yl]-3H-benzoimidazol-4-yl}-carbamic acid 2-methoxy-ethyl ester;

{2-[4-((S)-2-Hydroxy-2-phenyl-ethylamino)-2-oxo-1,2-dihydro-pyridin-3-yl]-3H-benzoimidazol-4-yl}-carbamic acid 2,2,2-trichloro-1,1-dimethyl-ethyl ester;

{2-[4-((S)-2-Hydroxy-2-phenyl-ethylamino)-2-oxo-1,2-dihydro-pyridin-3-yl]-3H-benzoimidazol-4-yl}-carbamic acid phenyl ester;

{2-[4-((S)-2-Hydroxy-2-phenyl-ethylamino)-2-oxo-1,2-dihydro-pyridin-3-yl]-3H-benzoimidazol-4-yl}-carbamic acid allyl ester;

{2-[4-((S)-2-Hydroxy-2-phenyl-ethylamino)-2-oxo-1,2-dihydro-pyridin-3-yl]-3H-benzoimidazol-4-yl}-carbamic acid isopropyl ester; and (2-{4-[(S)-2-(3-Chloro-phenyl)-2-hydroxy-ethylamino]-2-oxo-1,2-dihydro-pyridin-3-yl}-1H-benzoimidazol-4-yl)-carbamic acid methylester.

Another embodiment of the invention are the compounds according to formula I, characterized in that $R^1$ is —NR—$R^3$.

Another embodiment of the invention are the compounds according to formula I, characterized in that $R^1$ is —NR—$R^3$;

$R^3$ is a) —$(CH_2)_n$—$(O)_m$-phenyl, wherein the phenyl is unsubstituted or substituted one or two times independently by —O—$CH_3$, fluorine, chlorine, trifluoromethyl or trifluoromethoxy; with the proviso that if n is 0, m is also 0.

b) alkyl, wherein the alkyl is unsubstituted or substituted one to three times independently by —O—$CH_3$ or chlorine;

m is 0; and n is 0 or 1.

Such compounds, for example, may be selected from the group consisting of:

1-(3-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea;

1-{2-[4-((S)-2-Hydroxy-2-phenyl-ethylamino)-2-oxo-1,2-dihydro-pyridin-3-yl]-3H-benzoimidazol-4-yl}-3-(4-methoxy-phenyl)-urea;

1-(4-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea;

1-{2-[4-((S)-2-Hydroxy-2-phenyl-ethylamino)-2-oxo-1,2-dihydro-pyridin-3-yl]-3H-benzoimidazol-4-yl}-3-(4-trifluoromethoxy-phenyl)-urea;

1-{2-[4-((S)-2-Hydroxy-2-phenyl-ethylamino)-2-oxo-1,2-dihydro-pyridin-3-yl]-3H-benzoimidazol-4-yl}-3-phenyl-urea;

1-{2-[4-((S)-2-Hydroxy-2-phenyl-ethylamino)-2-oxo-1,2-dihydro-pyridin-3-yl]-3H-benzoimidazol-4-yl}-3-(3-methoxy-phenyl)-urea;

1-Benzyl-3-{2-[4-((S)-2-hydroxy-2-phenyl-ethylamino)-2-oxo-1,2-dihydro-pyridin-3-yl]-3H-benzoimidazol-4-yl}-urea; and 1-(2-Chloro-phenyl)-3-(2-{4-[(S)-2-(3-chloro-phenyl)-2-hydroxy-ethylamino]-2-oxo-1,2-dihydro-pyridin-3-yl}-1H-benzoimidazol-4-yl)-urea.

Another embodiment is a process for the preparation of the compounds of formula I by reacting a compound of formula III, formula III wherein R² has the meaning of formula I as defined above,
with a compound of formula IV, formula V or formula VI

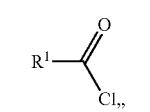
formula IV

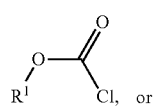
formula V

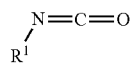
formula VI wherein R¹ has the meaning of formula I as defined above,
to give the compounds of formula I, formula I

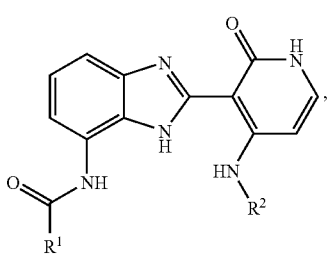

wherein R¹ and R² have the meaning of formula I as defined above.

The benzimidazole amido derivatives compounds of formula I, or a pharmaceutically acceptable salt thereof, which are subject of the present invention, may be prepared by any process known to be applicable to the preparation of chemically-related compounds. Such processes, when used to prepare a compound of the formula I, or a pharmaceutically-acceptable salt thereof, are illustrated by the following representative scheme 1 and examples in which, unless otherwise stated, R¹ and R² have the significance given herein before for formula I. Necessary starting materials are either commercially available or they may be obtained by standard procedures of organic chemistry. The preparation of such starting materials is described within the accompanying examples or in the literature cited below with respect to scheme 1. Alternatively necessary starting materials are obtainable by analogous procedures to those illustrated which are within the ordinary skill of an organic chemist.

Scheme 1:

In scheme 1 the preparation of the compounds of formula I is described starting from 3-Nitro-benzene-1,2-diamine (1) and 4-Iodo-2-methoxy-pyridine-3-carbaldehyde (2).

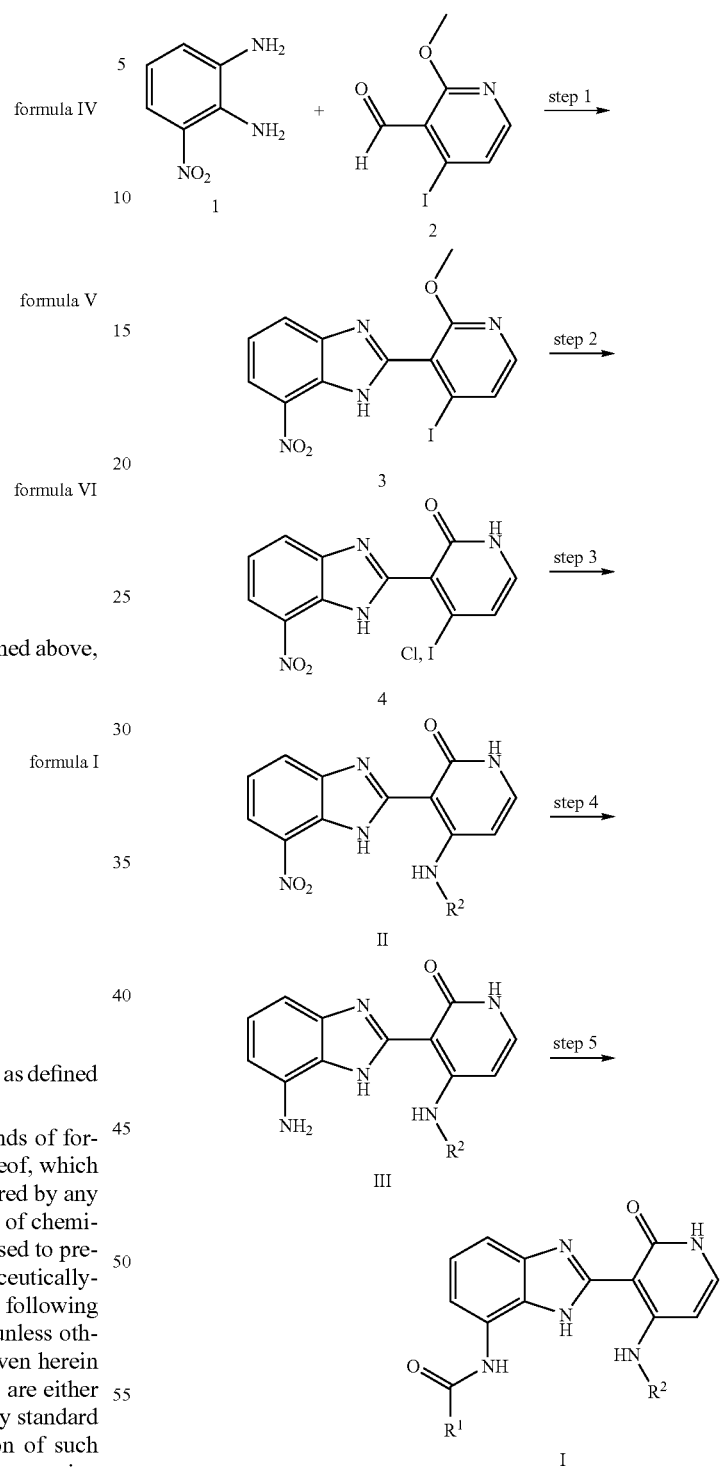

In scheme 1, R¹ and R² have the significance as given above for formula I.

Step 1:

In Step 1, 3-Nitro-benzene-1,2-diamine (1) and 4-Iodo-2-methoxy-pyridine-3-carbaldhyde (2) are condensed to 2-(4-Iodo-2-methoxy-pyridin-3-yl)-7-nitro-1H-benzoimidazole (3). The condensation is usually performed in the presence of dehydrating agents such as sulfur and the like under heating without or with inert solvents such as DMF or the like.

Step 2:

In Step 2,2-(4-Iodo-2-methoxy-pyridin-3-yl)-7-nitro-1H-benzoimidazole (3) is converted to a mixture of 4-Iodo-3-(7-nitro-1H-benzoimidazol-2-yl)-1H-pyridin-2-one and 4-Chloro-3-(7-nitro-1H-benzoimidazol-2-yl)-1H-pyridin-2-one (4) using concentrated HCl in inert solvents such dioxane and the like at temperatures between 25 an 80° C.

Step 3:

In Step 3, the iodo or chloro residue on the pyridone of the mixture of 4-Iodo-3-(7-nitro-1H-benzoimidazol-2-yl)-1H-pyridin-2-one and 4-Chloro-3-(7-nitro-1H-benzoimidazol-2-yl)-1H-pyridin-2-one (4) is substituted by an amine of formula $R^2$—$NH_2$ to give the corresponding amino-substituted pyridone derivatives of formula II. The reaction is carried in the presence of a non-nucleophilic base such as triethylamine, di-isopropyl-ethyl-amine and the like, in inert solvents such as acetonitrile, tetrahydrofuran, DMF, and the like at temperatures between 50 and 100° C.

Step 4:

The reduction of the nitro group of compounds of formula II to the amines of formula III to give the literature known amino-azaindole VIa is accomplished by heterogeneous hydrogenation with Platinum oxide as the catalyst, in an inert solvent like tetrahydrofuran (THF) at room temperature. Alternatively, a homogeneous hydrogenation with a Pd catalyst and triethyl ammonium formate in a solvent like methanol at reflux conditions may be applied. The reduction can also be carried out with base metals like iron or tin in acidic media like acetic acid or aqueous HCl, from room temperature to 120° C. Another suitable reductant would be ammonium sulfide in water or methanol, or tin (II) chloride in dimethylformamide (DMF) or in aqueous HCl.

Step 5:

In step 5, the amines of formula III are converted either to their corresponding amides using Method A or B as described in the examples by reaction with an activate carboxylic acid (e.g. chloride) in the presence of base such as triethylamine, di-isopropyl-ethyl-amine and the like. Alternatively the carboxylic acid can be activated in situ using an activating agents like 1-(3-dimethylaminopropyl)-3-ethylcarbodiimide (EDC) (or dicyclohexylcarbodiimide (DCC)), hydroxybenzotriazole (HOBt) with or without di-isopropylethylamine (DIPEA) in an inert solvent.

Or the amines of formula III are converted to their corresponding carbamates using Method C as described in the examples by reaction with the corresponding chloroformates in the presence of base such as pyridine, triethylamine, di-isopropyl-ethyl-amine and the like. Alternatively phosgene or triphosgen together with the corresponding hydroxy derivative can be used to generate the corresponding chloroformate as intermediate which is the reacted with the amine of formula III.

Or the amines of formula III are converted to their corresponding ureas using Method D as described in the examples by reaction with the corresponding isocyanate.

Pharmaceutical compositions containing a compound of the present invention or a pharmaceutically acceptable salt thereof and a pharmaceutically acceptable carrier are an object of the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

In accordance with the invention the compounds of the present invention as well as their pharmaceutically acceptable salts are useful in the control or prevention of illnesses. Based on their protein kinase activity and their antiproliferative activity, said compounds are useful for the treatment of diseases such as cancer in humans or animals and for the production of corresponding pharmaceutical compositions. The dosage depends on various factors such as manner of administration, species, age and/or individual state of health.

An embodiment of the invention is a pharmaceutical composition, containing one or more compounds according to formula I as active ingredients, together with pharmaceutically acceptable carriers.

Another embodiment of the invention is a pharmaceutical composition, containing one or more compounds according to formula I as active ingredients, for the inhibition of tumor growth.

Another embodiment of the invention is a pharmaceutical composition, containing one or more compounds according to formula I as active ingredients, for the treatment of cancer.

Another embodiment of the invention is a pharmaceutical composition containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a pharmaceutical composition containing one or more compounds of formula I as active ingredients together with pharmaceutically acceptable carriers for the treatment of acute-myelogenous leukemia (AML), acute lymphocytic leukemia (ALL) and gastrointestinal stromal tumor (GIST).

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of pharmaceutical compositions for the treatment of acute-myelogenous leukemia (AML), acute lymphocytic leukemia (ALL) and gastrointestinal stromal tumor (GIST).

Another embodiment of the invention is the use of the compounds of formula I as anti-proliferating agents.

Another embodiment of the invention is the use of one or more compounds of formula I for the treatment of cancer.

Another embodiment of the invention is a method of treating cancer comprising administering to a person in need thereof a therapeutically effective amount of a compound of formula I.

Another embodiment of the invention is a method of treating cancer comprising administering to a person in need thereof a therapeutically effective amount of a compound of formula I, wherein the cancer is colorectal cancer, breast cancer, lung cancer, prostate cancer, pancreatic cancer, gastric cancer, bladder cancer, ovarian cancer, melanoma, neuroblastoma, cervical cancer, kidney cancer or renal cancer, leukemia, or lymphoma.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid, citric acid, ascorbic acid and the like. The chemical modification of a pharmaceutical compound (I.e. a drug) into a salt is a technique well known to pharmaceutical chemists to obtain improved physical and chemical stability, hygroscopicity, flowability and solubility of compounds (see, e.g., Stahl, P. H. and Wermuth, G. (editors), Handbook of Pharmaceutical Salts, Verlag Helvetica Chimica Acta (VHCA), Zürich (2002), or Bastin, R. J., et al., Organic Proc. Res. Dev. 4 (2000) 427-435).

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases (HPLC: High Performance Liquid Chromatography) which are commercially available.

Pharmacological Activity

The compounds of formula I and their pharmaceutically acceptable salts possess valuable pharmacological properties. It has been found that said compounds show activity as inhibitors and also show anti-proliferative activity. Consequently the compounds of the present invention are useful in the therapy and/or prevention of proliferative diseases and illnesses with known over-expression of kinases.

Antiproliferative Activity

The activity of the present compounds as antiproliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) were cultivated in RPMI 1640 medium with GlutaMAX™ I (Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:
Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
HCT116 (ATCC-No. CCl-247): 1000 cells in 60 µl per well of 384 well plate (Greiner 781098, µClear-plate white)
After seeding incubate plates 24 h at 37° C., 5% $CO_2$ 2nd. Day: Induction (Treatment with Compounds, 10 Concentrations):
In order to achieve a final concentration of 30 µM as highest concentration 3.5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a-e) as described here below:

a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3.5 µl compound dilution to 163 µl media)
e) add 10 µl of every concentration to 60 µl media in the cell plate resulting in final concentration of DMSO: 0.3% in every well and resulting in 10 final concentration of compounds ranging from 30 µM to 0.0015 µM.
Each compound is tested in triplicate.
Incubate 120 h (5 days) at 37° C., 5% $CO_2$ Analysis:
Add 30 µl CellTiter-Glo™ Reagent (prepared from CellTiter-Glo™ Buffer and
CellTiter-Glo™ Substrate (lyophilized) purchased from Promega) per well,
shake 15 minutes at room temperature
incubate further 45 minutes at room temperature without shaking Measurement:
Victor 2 scanning multiwell spectrophotometer (Wallac), Luminescence mode (0.5 sec/read, 477 nm)
Determine IC50 using a non-linear curve fit (XLfit software (ID Business Solution Ltd., Guilford, Surrey, UK))

With all compounds a significant inhibition of HCT 116 cell viability was detected, which is exemplified by the compounds shown in Table 1.

TABLE 1

| Example No. | IC50 HCT 116 [µM] |
| --- | --- |
| A-1 | 1.36 |
| B-15 | 6.92 |
| C-5 | 2.78 |
| D-3 | 3.61 |
| A-3, A-4, A-5, A-6, A-7, A-8, A-11, A-12, A-15, A-16, A-17, A-18, B-1, B-2, B-3, B-5, B-6, B-8, B-9, B-10, B-11, B-12, B-13, B-16, B-18, B-19, C-1, C-2, C-3, C-6, C-7, D-1, D-2, D-4, D-5, D-6, D-7, D-8, | 1.00-15.00 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:

a) Tablet Formulation (Wet Granulation):

| Item | Ingredients | Mg/tablet | | | |
|---|---|---|---|---|---|
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | Mg/capsule | | | |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Micro Suspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminum foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenize.

The following examples are provided to aid the understanding of the present invention, the true scope of which is set forth in the appended claims. It is understood that modifications can be made in the procedures set forth without departing from the spirit of the invention.

EXPERIMENTAL PROCEDURES

Starting Material and Intermediates 2-(4-Iodo-2-methoxy-pyridin-3-yl)-7-nitro-1H-benzoimidazole 3-Nitro-benzene-1,2-diamine (0.153 g, 1.0 mmol), 4-Iodo-2-methoxy-pyridine-3-carbaldehyde (0.263 g, 1.0 mmol) and sulfur (0.032 g, 1.0 mmol) were heated at 160° for 60 min. The resulting slurry was purred on ice water (100 ml). Precipitates were collected by filtration and dried in vacuum to yield the desired product (0.40 g, quant.) which was used without any further purification.

Mixture of 4-Iodo-3-(7-nitro-1H-benzoimidazol-2-yl)-1H-pyridin-2-one and 4-Chloro-3-(7-nitro-1H-benzoimidazol-2-yl)-1H-pyridin-2-one Conc. HCl (4 ml of a 37% aqueous solution) was added to 2-(4-Iodo-2-methoxy-pyridin-3-yl)-7-nitro-1H-benzoimidazole (0.40 g, 1.0 mmol) in dioxane (40 ml) The mixture was stirred at 50° C. for 2 h. $H_2O$, ethyl acetate and a satd. aqueous solution of $NaHCO_3$ were added. The mixture was extracted with ethyl acetate. The combined organic phases were dried under reduced pressure and the resulting raw product was purified by silica gel chromatography (hexane) to give the desired mixture of 4-Iodo-3-(7-nitro-1H-benzoimidazol-2-yl)-1H-pyridin-2-one and 4-Chloro-3-(7-nitro-1H-benzoimidazol-2-yl)-1H-pyridin-2-one.

General Method for the Preparation of the Intermediates of Formula II (Step 3, Scheme 1) with the Representative Example of 3-(4-Nitro-1H-benzoimidazol-2-yl)-4-[(pyridin-2-ylmethyl)-amino]-1H-pyridin-2-one 3-(4-Nitro-1H-benzoimidazol-2-yl)-4-[(pyridin-2-ylmethyl)-amino]-1H-pyridin-2-one Triethylamine (0.78 g, 7.8 mmol) was added to a solution of the mixture of 4-Iodo-3-(7-nitro-1H-benzoimidazol-2-yl)-1H-pyridin-2-one and 4-Chloro-3-(7-nitro-1H-benzoimidazol-2-yl)-1H-pyridin-2-one (1.7 mmol) as obtained above, and 2-(aminomethyl)pyridine (0.28 g, 2.6 mmol), in acetonitrile (15 ml) and the reaction heated to 80° C. After 30 minutes the reaction was cooled to room temperature and the solid isolated by filtration and washed with acetonitrile water (1:1, 5 ml) to give the desired product (0.58 g, 94%).

1H NMR (400 MHz, DMSO-d6) d ppm 13.93 (1H, s), 11.5 (1H, br. s.), 11.12 (1H, t), 8.63 (1H, d), 8.10-8.06 (2H, m), 7.81 (1H, dt), 7.44-7.41 (3H, m), 7.34 (1H, dd), 6.18 (1H, d), 4.86 (2H, d).

General Method for the Preparation of the Intermediates of Formula II (Step 4, Scheme 1) with the Representative Example of 3-(4-Amino-1H-benzoimidazol-2-yl)-4-[(pyridin-2-ylmethyl)-amino]-1H-pyridin-2-one 3-(4-Amino-1H-benzoimidazol-2-yl)-4-[(pyridin-2-ylmethyl)-amino]-1H-pyridin-2-one Platinum oxide (0.146 g, 0.65 mmol) was added to a stirred solution of 3-(4-nitro-1H-benzoimidazol-2-yl)-4-[(pyridin-2-ylmethyl)-amino]-1H-pyridin-2-one in methanol (12 ml) and tetrahydrofuran (12 ml). The reaction was purged with nitrogen three times and the atmosphere replaced with hydrogen and the reaction stirred at room temperature. After 72 hours the reaction was recharged with platinum oxide (0.146 g, 0.65 mmol) and hydrogen and stirred for a further 24 hours. The reaction was filtered through Celite and the filter cake washed with tetrahydrofuran and methanol. The solvent was concentrated under reduced pressure to give the desired crude aniline (0.610 g, 113%), which was used without further purification.

Final Products

Method A, Example 1 (A-1)

3-Cyano-N-(2-[2-oxo-4-1 (pyridin-2-ylmethyl)-amino]-1,2-dihydro-pyridin-1H-benzoimidazol-4-yl)-benzamide Triethylamine (0.082 g, 0.61 mmol), was added to a solution of 3-(4-amino-1H-benzoimidazol-2-yl)-4-[(pyridin-2-ylmethyl)-amino]-1H-pyridin-2-one (0.081 g, 0.245 mmol) (Prepared according to the general method for the intermediates of formula II and III above) and 3-cyanobenzoyl chloride (0.081 g 0.49 mmol) in THF (2 ml) and the reaction stirred at room temperature. After 20 hours methanolic ammonia was added (2 ml) and the reaction stirred for a further 20 hours. The reaction mixture was concentrated under reduced pressure and HCl, (2M in dioxane, 2 ml) was added. After 2 hours the reaction was concentrated under reduced pressure and the crude solid purified by preparative HPLC (neutral conditions) to give the amide (2.7 mg, 2.4%).

Tr=1.78 min, m/z (ES+) (M+H)$^+$462.

1H NMR (400 MHz, DMSO-d6) d ppm 12.93-12.91 (1H, m), 11.51-11.43 (1H, m), 11.27-11.16 (1H, m), 10.89-10.33 (1H, m), 8.62-8.25 (3H, m), 8.13-8.03 (1H, m), 7.83-7.07 (8H, m), 6.14-6.10 (1H, m), 4.83-4.77 (2H, m).

Method A, Example 2 (A-2)

N-[2-(4-Benzylamino-2-oxo-1,2-dihydro-pyridin-3-yl)-3H-benzoimidazol-4-yl]-2,4-difluoro-benzamide Tr=4.81 min, m/z (ES+) (M+H)$^+$472

Method A, Example 3 (A-3)

N-[2-(4-Benzylamino-2-oxo-1,2-dihydro-pyridin-3-yl)-3H-benzoimidazol-4-yl]-4-methoxy-benzamide Tr=4.48 min, m/z (ES+) (M+H)$^+$466

Method A, Example 4 (A-4)

N-[2-(4-Benzylamino-2-oxo-1,2-dihydro-pyridin-3-yl)-3H-benzoimidazol-4-yl]-benzamide Tr=2.24 min, m/z (ES+) (M+H)$^+$436

Method A, Example 5 (A-5)

N-(2-{2-oxo-4-[(pyridin-2-ylmethyl)-amino]-1,2-dihydro-pyridin-3-yl}-3H-benzoimidazol-4-yl)-benzamide Tr=1.74 min, m/z (ES+) (M+H)$^+$436

Method A, Example 6 (A-6)

4-Methoxy-N-(2-{2-oxo-4-[(pyridin-2-ylmethyl)-amino]-1,2-dihydro-pyridin-3-yl}-3H-benzoimidazol-4-yl)-benzamide Tr=1.81 min, m/z (ES+) (M+H)$^+$467

Method A, Example 7 (A-7)

4-Chloro-N-(2-{2-oxo-4-[(pyridin-2-ylmethyl)-amino]-1,2-dihydro-pyridin-3-yl}-3H-benzoimidazol-4-yl)-benzamide Tr=1.96 min, m/z (ES+) (M+H)$^+$471+473

Method A, Example 8 (A-8)

N-{2-[4-(3-Chloro-benzylamino)-2-oxo-1,2-dihydro-pyridin-3-yl]-3H-benzoimidazol-4-yl}-4-methoxy-benzamide 1H NMR (400 MHz, DMSO-d6) d ppm 11.29 (1H, d), 10.72 (1H, s), 10.40 (1H, s), 8.04 (2H, d), 7.59-7.54 (1H, m), 7.48-7.46 (2H, m), 7.38-7.33 (4H, m), 7.25-7.21 (1H, m), 7.10-7.05 (2H, m), 6.07 (1H, d), 4.72 (2H, s), 3.85 (3H, s)

Method A, Example 9 (A-9)

4-Chloro-N-{2-[4-(3-chloro-benzylamino)-2-oxo-1,2-dihydro-pyridin-3-yl]-3H-benzoimidazol-4-yl}-benzamide 1H NMR (400 MHz, DMSO-d6) d ppm 11.26 (1H, d), 11.03 (1H, s), 10.59 (1H, s), 8.04 (2H, d), 7.61-7.44 (5H, m), 7.39-7.29 (4H, m), 7.23-7.19 (1H, m), 6.09 (1H, d), 4.73 (2H, s)

Method A, Example 10 (A-10)

N-{2-[4-(3-Chloro-benzylamino)-2-oxo-1,2-dihydro-pyridin-3-yl]-3H-benzoimidazol-4-yl}-2,4-difluoro-benzamide 1H NMR (400 MHz, DMSO-d6) d ppm 11.34 (1H, s), 11.26 (1H, s), 7.91-7.87 (1H, s), 7.47-7.15 (11H, m), 6.09 (1H, m), 4.76 (2H, d).

Method A, Example 11 (A-11)

3-Chloro-N-[2-[4-(2-hydroxy-2-phenyl-ethylamino)-2-oxo-1,2-dihydro-pyridin-3-yl]-3H-benzoimidazol-4-yl]-benzamide Tr=2.30 min, m/z (ES+) (M+H)$^+$500+502

Method A, Example 12 (A-12)

4-Fluoro-N-{2-[4-((S)-2-hydroxy-2-phenyl-ethylamino)-2-oxo-1,2-dihydro-pyridin-3-yl]-3H-benzoimidazol-4-yl}-benzamide Tr=2.20 min, m/z (ES+) (M+H)$^+$484

Method A, Example 13 (A-13)

3,4-Dichloro-N-{2-[4-((S)-2-hydroxy-2-phenyl-ethylamino)-2-oxo-1,2-dihydro-pyridin-3-yl]-3H-benzoimidazol-4-yl}-benzamide 1H NMR (400 MHz, DMSO-d6) d ppm 12.82 (1H, d), 11.11 (1H, s), 10.80 (1H, s), 8.29 (1H, d), 8.04 (1H, d), 7.82-7.80 (1H, m), 7.46-7.16 (9H, m), 6.18 (1H, d), 7.10-4.88 (1H, s), 3.63-3.62 (2H, m).

Method A, Example 14 (A-14)

N-{2-[4-((S)-2-Hydroxy-2-phenyl-ethylamino)-2-oxo-1,2-dihydro-pyridin-3-yl]-3H-benzoimidazol-4-yl}-3-phenyl-propionamide Tr=2.25 min, m/z (ES+) (M+H)$^+$494

Method A, Example 15 (A-15)

N-{2-[4-((S)-2-Hydroxy-2-phenyl-ethylamino)-2-oxo-1,2-dihydro-pyridin-3-yl]-3H-benzoimidazol-4-yl}-4-trifluoromethyl-benzamide Tr=2.39 min, m/z (ES+) (M+H)$^+$534

Method A, Example 16 (A-16)

N-[2-(4-Benzylamino-2-oxo-1,2-dihydro-pyridin-3-yl)-3H-benzoimidazol-4-yl]-2-methoxy-benzamide Tr=2.34 min, m/z (ES+) (M+H)$^+$466

Method A, Example 17 (A-17)

N-[2-(4-Benzylamino-2-oxo-1,2-dihydro-pyridin-3-yl)-3H-benzoimidazol-4-yl]-2-chloro-benzamide Tr=2.28 min, m/z (ES+) (M+H)$^+$470+472

Method A, Example 18 (A-18)

N-[2-(4-Benzylamino-2-oxo-1,2-dihydro-pyridin-3-yl)-3H-benzoimidazol-4-yl]-4-chloro-benzamide Tr=2.38 min, m/z (ES+) (M+H)$^+$470+472

Method B, Example 1 (B-1)

N-{2-[4-((S)-2-Hydroxy-2-phenyl-ethylamino)-2-oxo-1,2-dihydro-pyridin-3-yl]-3H-benzoimidazol-4-yl}-2-phenyl-acetamide Triethylamine (0.058 g, 0.416 mmol) was added to a solution of 3-(7-amino-1H-benzoimidazol-2-yl)-4-((S)-2-hydroxy-2-phenyl-ethylamino)-1H-pyridin-2-one (0.060 g, 0.166 mmol) (Prepared according to the general method for the intermediates of formula II and III above) and phenylacetyl chloride (0.051 g 0.32 mmol) in THF (2 ml) and the reaction stirred at room temperature. After 20 hours methanolic ammonia was added (5 ml) and the reaction stirred for a further 20 hours. The reaction mixture was concentrated under reduced pressure and the crude solid washed with acetonitrile water (1:1; 10 ml) to give the desired product (0.034 g; 43%).

Tr=2.15 min, m/z (ES+) (M+H)$^+$480

Method B, Example 2 (B-2)

N-{2-[4-(3-Chloro-benzylamino)-2-oxo-1,2-dihydro-pyridin-3-yl]-3H-benzoimidazol-4-yl}-benzamide 1H NMR (400 MHz, DMSO-d6) d ppm 11.26-11.10 (2H, m), 10.53 (1H, s), 8.02 (2H, d), 7.64-7.17 (11H, m), 6.10 (1H, d) 4.74 (2H, s).

Method B, Example 3 (B-3)

N-{2-[4-((S)-2-Hydroxy-2-phenyl-ethylamino)-2-oxo-1,2-dihydro-pyridin-3-yl]-3H-benzoimidazol-4-yl}-2,2-dimethyl-propionamide Tr=2.07 min, m/z (ES+) (M+H)$^+$446

Method B, Example 4 (B-4)

N-{2-[4-((S)-2-Hydroxy-2-phenyl-ethylamino)-2-oxo-1,2-dihydro-pyridin-3-yl]-3H-benzoimidazol-4-yl}-4-methoxy-benzamide Tr=2.13 min, m/z (ES+) (M+H)$^+$496

Method B, Example 5 (B-5)

N-{2-[4-((S)-2-Hydroxy-2-phenyl-ethylamino)-2-oxo-1,2-dihydro-pyridin-3-yl]-3H-benzoimidazol-4-yl}-3-trifluoromethyl-benzamide Tr=2.33 min, m/z (ES+) (M+H)$^+$534

Method B, Example 6 (B-6)

N-{2-[4-((S)-2-Hydroxy-2-phenyl-ethylamino)-2-oxo-1,2-dihydro-pyridin-3-yl]-3H-benzoimidazol-4-yl}-2-phenoxy-acetamide Tr=2.20 min, m/z (ES+) (M+H)$^+$496

Method B, Example 7 (B-7)

N-{2-[4-((S)-2-Hydroxy-2-phenyl-ethylamino)-2-oxo-1,2-dihydro-pyridin-3-yl]-3H-benzoimidazol-4-yl}-3,3-dimethyl-butyramide Tr=2.20 min, m/z (ES+) (M+H)$^+$460

Method B, Example 8 (B-8)

Cyclopropanecarboxylic acid {2-[4-((S)-2-hydroxy-2-phenyl-ethylamino)-2-oxo-1,2-dihydro-pyridin-3-yl]-3H-benzoimidazol-4-yl}-amide Tr=1.97 min, m/z (ES+) (M+H)$^+$430

Method B, Example 9 (B-9)

2-Fluoro-N-{2-[4-((S)-2-hydroxy-2-phenyl-ethylamino)-2-oxo-1,2-dihydro-pyridin-3-yl]-3H-benzoimidazol-4-yl}-benzamide Tr=2.18 min, m/z (ES+) (M+H)$^+$484

Method B, Example 10 (B-10)

2-Chloro-N-{2-[4-(2-hydroxy-2-phenyl-ethylamino)-2-oxo-1,2-dihydro-pyridin-3-yl]-3H-benzoimidazol-4-yl}-benzamide Tr=2.15 min, m/z (ES+) (M+H)$^+$500+502

Method B, Example 11 (B-11)

2-(4-Chloro-phenoxy)-N-{2-[4-((S)-2-hydroxy-2-phenyl-ethylamino)-2-oxo-1,2-dihydro-pyridin-3-yl]-3H-benzoimidazol-4-yl}-acetamide Tr=2.33 min, m/z (ES+) (M+H)$^+$530+532

Method B, Example 12 (B-12)

3-Cyano-N-{2-[4-((S)-2-hydroxy-2-phenyl-ethylamino)-2-oxo-1,2-dihydro-pyridin-3-yl]-3H-benzoimidazol-4-yl}-benzamide Tr=2.13 min, m/z (ES+) (M+H)$^+$491

Method B, Example 13 (B-13)

N-{2-[4-((S)-2-Hydroxy-2-phenyl-ethylamino)-2-oxo-1,2-dihydro-pyridin-3-yl]-3H-benzoimidazol-4-yl}-2-methoxy-acetamide 1H NMR (400 MHz, DMSO-d6) d ppm 12.94-12.90 (1H, m), 11.19-11.16 (1H, m), 11.05-11.01 (1H, m), 10.83-9.71 (1H, m), 8.04-7.81 (2H, m), 7.55-7.13 (13H, m), 6.24-6.15 (1H, m), 5.78-5.58 (1H, m), 4.92-4.81 (1H, m), 3.65-3.53 (1H, m), 3.47-3.44 (2H, m).

Method B, Example 14 (B-14)

2,4-Difluoro-N-{2-[4-((S)-2-hydroxy-2-phenyl-ethylamino)-2-oxo-1,2-dihydro-pyridin-3-yl]-3H-benzoimidazol-4-yl}-benzamide 1H NMR (400 MHz, DMSO-d6) d ppm 12.94-12.90 (1H, m), 11.19-11.16 (1H, m), 11.05-11.01 (1H, m), 10.83-9.71 (1H, m), 8.04-7.81 (2H, m), 7.55-7.13 (13H, m), 6.24-6.15 (1H, m), 5.78-5.58 (1H, m), 4.92-4.81 (1H, m), 3.65-3.53 (1H, m), 3.47-3.44 (2H, m).

Method B, Example 15 (B-15)

3-Fluoro-N-{2-[4-((S)-2-hydroxy-2-phenyl-ethylamino)-2-oxo-1,2-dihydro-pyridin-3-yl]-3H-benzoimidazol-4-yl}-benzamide Tr=2.20 min, m/z (ES+) (M+H)$^+$484

Method B, Example 16 (B-16)

2,4-Dichloro-N-{2-[4-((S)-2-hydroxy-2-phenyl-ethylamino)-2-oxo-1,2-dihydro-pyridin-3-yl}-3H-benzoimidazol-4-yl]-benzamide 1H NMR (400 MHz, DMSO-d6) d ppm 12.94-12.87 (1H, m), 11.39-11.12 (1H, m), 11.08-11.03 (1H, m), 10.95-9.90 (1H, m), 7.95-7.78 (1H, m), 7.73-7.59 (2H, m), 7.54-7.15 (10H, m), 6.21-6.14 (1H, m), 5.78-5.51 (1H, m), 4.91-4.79 (1H, m), 3.68-3.52 (2H, m).

Method B, Example 17 (B-17)

N-{2-[4-((S)-2-Hydroxy-2-phenyl-ethylamino)-2-oxo-1,2-dihydro-pyridin-3-yl]-3H-benzoimidazol-4-yl}-3-methoxy-benzamide Tr=2.16 min, m/z (ES+) (M+H)$^+$496

Method B, Example 18

N-{2-[4-((S)-2-Hydroxy-2-phenyl-ethylamino)-2-oxo-1,2-dihydro-pyridin-3-yl]-3H-benzoimidazol-4-yl}-3-methoxy-benzamide Tr=2.12 min, m/z (ES+) (M+H)$^+$491

Method B, Example 19

Furan-2-carboxylic acid {2-[4-((S)-2-hydroxy-2-phenyl-ethylamino)-2-oxo-1,2-dihydro-pyridin-3-yl]-3H-benzoimidazol-4-yl}-amide Tr=2.02 min, m/z (ES+) (M+H)$^+$456

Method C, Example 1 (C-1)

{2-[4-((S)-2-Hydroxy-2-phenyl-ethylamino)-2-oxo-1,2-dihydro-pyridin-3-yl]-3H-benzoimidazol-4-yl}-carbamic acid 4-methoxy-phenyl ester Pyridine (2.0 ml) was added to a solution of 3-(7-amino-1H-benzoimidazol-2-yl)-4-((S)-2-hydroxy-2-phenyl-ethylamino)-1H-pyridin-2-one (0.060 g, 0.166 mmol) (Prepared according to the general method for the intermediates of formula II and III above) and 4-methoxyphenyl chloroformate (0.062 g, 0.32 mmol) in THF (2 ml) and the reaction stirred at room temperature. After 20 hours the reaction was concentrated and the crude mixture was purified by column chromatography (1-2% methanol, dichloromethane) to give the desired product (0.028 g; 33%).

Tr=2.20 min, m/z (ES+) (M+H)$^+$512

Method C, Example 2(C-2)

{2-[4-((S)-2-Hydroxy-2-phenyl-ethylamino)-2-oxo-1,2-dihydro-pyridin-3-yl]-3H-benzoimidazol-4-yl}-carbamic acid 2-methoxy-ethyl ester Tr=1.98 min, m/z (ES+) (M+H)$^+$464

Method C, Example 3(C-3)

{2-[4-((S)-2-Hydroxy-2-phenyl-ethylamino)-2-oxo-1,2-dihydro-pyridin-3-yl]-3H-benzoimidazol-4-yl}-carbamic acid 2,2,2-trichloro-1,1-dimethyl-ethyl ester Tr=2.54 min, m/z (ES+) (M+H)$^+$564+566

Method C, Example 4(C-4)

{2-[4-((S)-2-Hydroxy-2-phenyl-ethylamino)-2-oxo-1,2-dihydro-pyridin-3-yl]-3H-benzoimidazol-4-yl}-carbamic acid phenyl ester Tr=2.21 min, m/z (ES+) (M+H)$^+$482

Method C, Example 5(C-5)

{2-[4-((S)-2-Hydroxy-2-phenyl-ethylamino)-2-oxo-1,2-dihydro-pyridin-3-yl]-3H-benzoimidazol-4-yl}-carbamic acid allyl ester Tr=2.14 min, m/z (ES+) (M+H)$^+$446

Method C, Example 6 (C-6)

{2-[4-((S)-2-Hydroxy-2-phenyl-ethylamino)-2-oxo-1,2-dihydro-pyridin-3-yl]-3H-benzoimidazol-4-yl}-carbamic acid isopropyl ester Tr=2.18 min, m/z (ES+) (M+H)$^+$448

Method C, Example 7 (C-7)

(2-{4-[(S)-2-(3-Chloro-phenyl)-2-hydroxy-ethylamino]-2-oxo-1,2-dihydro-pyridin-3-yl}-1H-benzoimidazol-4-yl)-carbamic acid methylester Tr=2.72 min, m/z (ES+) (M+H)$^+$454

Method D, Example 1 (D-1)

1-(3-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea 3-Fluorophenylisocyanate (0.023 g, 0.166 mmol) was added to a solution of 3-(7-amino-1H-benzoimidazol-2-yl)-4-((S)-2-hydroxy-2-phenyl-ethylamino)-1H-pyridin-2-one (0.060 g, 0.166 mmol) (Prepared according to the general method for the intermediates of formula II and III above) in DCM (4 ml) and the reaction stirred at room temperature. After 20 hours methanolic ammonia was added (5 ml) and the reaction stirred for a further 20 hours. The reaction mixture was concentrated under reduced pressure and the crude solid washed with acetonitrile:water (1:1; 10 ml) to give the desired product (0.037 g; 45%).

1H NMR (400 MHz, DMSO-d6) d ppm 11.15 (1H, t), 10.92-9.86 (1H, m), 9.31-8.19 (2H, m), 7.61-7.49 (3H, m), 7.36-7.28 (5H, m), 7.24-7.15 (2H, m), 7.11-7.07 (1H, m), 7.04-6.77 (1H, m), 6.22 (1H, d), 4.92 (1H, m)

Method D, Example 2 (D-2)

1-{2-[4-((S)-2-Hydroxy-2-phenyl-ethylamino)-2-oxo-1,2-dihydro-pyridin-3-yl]-3H-benzoimidazol-4-yl}-3-(4-methoxy-phenyl)-urea Tr=2.11 min, m/z (ES+) (M+H)$^+$511

Method D, Example 3 (D-3)

1-(4-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea Tr=2.18 min, m/z (ES+) (M+H)$^+$499

Method D, Example 4 (D-4)

1-{2-[4-((S)-2-Hydroxy-2-phenyl-ethylamino)-2-oxo-1,2-dihydro-pyridin-3-yl]-3H-benzoimidazol-4-yl}-3-(4-trifluoromethoxy-phenyl)-urea Tr=2.45 min, m/z (ES+) (M+H)$^+$565

Method D, Example 5 (D-5)

1-{2-[4-((S)-2-Hydroxy-2-phenyl-ethylamino)-2-oxo-1,2-dihydro-pyridin-3-yl]-3H-benzoimidazol-4-yl}-3-phenyl-urea Tr=2.21 min, m/z (ES+) (M+H)$^+$481

Method D, Example 6 (D-6)

1-{2-[4-((S)-2-Hydroxy-2-phenyl-ethylamino)-2-oxo-1,2-dihydro-pyridin-3-yl]-3H-benzoimidazol-4-yl}-3-(3-methoxy-phenyl)-urea Tr=2.18 min, m/z (ES+) (M+H)$^+$511

Method D, Example 7 (D-7)

1-Benzyl-3-{2-[4-((S)-2-hydroxy-2-phenyl-ethylamino)-2-oxo-1,2-dihydro-pyridin-3-yl]-3H-benzoimidazol-4-yl}-urea Tr=2.12 min, m/z (ES+) (M+H)$^+$495

Method D, Example 8 (D-8)

1-(2-Chloro-phenyl)-3-(2-{4-[(S)-2-(3-chloro-phenyl)-2-hydroxy-ethylamino]-2-oxo-1,2-dihydro-pyridin-3-yl}-1H-benzoimidazol-4-yl)-urea Tr=4.38 min, m/z (ES+) (M+H)$^+$549

The invention claimed is:

1. A compound of formula I,

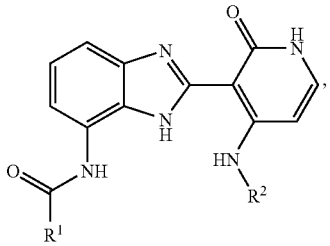

formula I wherein
R$^1$ is selected from the group consisting of: —R$^3$, —O—R$^3$ and —NR—R$^3$;
R$^2$ is —X—R$^4$;
R$^3$ is selected from the group consisting of:
 a) —(CH$_2$)$_n$—(O)$_m$-phenyl, wherein the phenyl is optionally substituted one to three times with the substitutents being each independently selected from the group consisting of: alkyl, —O-alkyl, halogen, cyano, —N(alkyl)$_2$, trifluoromethyl, and trifluoromethoxy; with the proviso that, if R$^1$ is O—R$^3$ or —NR—R$^3$ and n is 0, m is also 0;
 b) alkyl, wherein the alkyl is optionally substituted one to three times with the substituents being each independently selected from the group consisting of: —O-alkyl and halogen;
 c) alkenyl;
 d) heteroaryl; and
 e) (C$_3$-C$_6$) cycloalkyl;
R$^4$ is
 a) phenyl, wherein the phenyl is optionally substituted one to three times with the substitutents being each independently selected from the group consisting of: halogen, alkyl, —O-alkyl, —N(alkyl)$_2$, trifluoromethyl and trifluoromethoxy; or
 b) pyridyl;
X is (C$_1$-C$_3$)alkylene, wherein the alkylene is optionally substituted once or twice with the substitutents being each independently selected from the group consisting of: hydroxy, alkyl and halogen;
R is hydrogen or (C$_1$-C$_3$)alkyl;
m is 0 or 1; and
n is 0, 1 or 2;
or a pharmaceutically acceptable salt thereof.

2. A compound according to claim 1 characterized in that R$^3$ is selected from the group consisting of:
 a) —(CH$_2$)$_n$—(O)$_m$-phenyl, wherein the phenyl is optionally substituted one or two times with the substitutents being each independently selected from the group consisting of: —O—CH$_3$, cyano, fluorine, chlorine, trifluoromethyl and trifluoromethoxy; with the proviso that, if R$^1$ is —O—R$^3$, or —NR—R$^3$ and n is 0, m is also 0;
 b) alkyl, wherein the alkyl is optionally substituted one to three times with the substituents being each independently selected from the group consisting of: —O—CH$_3$ and chlorine;
 c) allyl;
 d) furanyl; and
 e) cyclopropyl;

R$^4$ is a) phenyl, wherein the phenyl is optionally substituted once by chlorine; or
 b) pyridyl;
X is (C$_1$-C$_3$)alkylene, wherein the alkylene is optionally substituted once by hydroxy;
R is hydrogen; and
n is 0 or 1.

3. A compound according to claim 1 characterized in that R$^1$ is —R$^3$ or —NR—R$^3$; and
R$^3$ is selected from the group consisting of:
 a) —(CH$_2$)$_n$—(O)$_m$-phenyl, wherein the phenyl is optionally substituted one or two times with the substitutents being each independently selected from the group consisting of: —O—CH$_3$, cyano, chlorine, trifluoromethyl and trifluoromethoxy; with the proviso that, if R$^1$ is —O—R$^3$, or —NR—R$^3$ and n is 0, m is also 0;
 b) alkyl, wherein the alkyl is substituted once by —O—CH$_3$;
 c) furanyl; and
 d) cyclopropyl.

4. A compound according to claim 1 characterized in that R$^1$ is —R$^3$.

5. A compound according to claim 4, selected from the group consisting of:
3-Cyano-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
N-[2-(4-Benzylamino-2-oxo-1,2-dihydro-pyridin-3-yl)-3H-benzoimidazol-4-yl]-2,4-difluoro-benzamide; compound with hydrochloric acid;
N-[2-(4-Benzylamino-2-oxo-1,2-dihydro-pyridin-3-yl)-3H-benzoimidazol-4-yl]-4-methoxy-benzamide; compound with hydrochloric acid;
N-[2-(4-Benzylamino-2-oxo-1,2-dihydro-pyridin-3-yl)-3H-benzoimidazol-4-yl]-benzamide; compound with hydrochloric acid;
N-(2-{2-Oxo-4-[(pyridin-2-ylmethyl)-amino]-1,2-dihydro-pyridin-3-yl}-3H-benzoimidazol-4-yl)-benzamide; compound with hydrochloric acid;
4-Methoxy-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
4-Chloro-N-(2-{2-oxo-4-[(pyridin-2-ylmethyl)-amino]-1,2-dihydro-pyridin-3-yl}-3H-benzoimidazol-4-yl)-benzamide; compound with hydrochloric acid;
N-{2-[4-(3-Chloro-benzylamino)-2-oxo-1,2-dihydro-pyridin-3-yl]-3H-benzoimidazol-4-yl}-4-methoxy-benzamide; compound with hydrochloric acid;
4-Chloro-N-{2-[4-(3 chloro-benzylamino)-2-oxo-1,2-dihydro-pyridin-3-yl]-3H-benzoimidazol-4-yl}-benzamide; compound with hydrochloric acid;
N-{2-[4-(3-Chloro-benzylamino)-2-oxo-1,2-dihydro-pyridin-3-yl]-3H-benzoimidazol-4-yl}-2,4-difluoro-benzamide; compound with hydrochloric acid;
3-Chloro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;
4-Fluoro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;
3,4-Dichloro-N-{2-[4-((S)-2-hydroxy-2-phenyl-ethylamino)-2-oxo-1,2-dihydro-pyridin-3-yl]-3H-benzoimidazol-4-yl}-benzamide; compound with hydrochloric acid;

N-{2-[4-((S)-2-Hydroxy-2-phenyl-ethylamino)-2-oxo-1,
2-dihydro-pyridin-3-yl]-3H-benzoimidazol-4-yl}-3-
phenyl-propionamide; compound with hydrochloric
acid;
N-{2-[4-((S)-2-Hydroxy-2-phenyl-ethylamino)-2-oxo-1,
2-dihydro-pyridin-3-yl]-3H-benzoimidazol-4-yl}-4-
trifluoromethyl-benzamide; compound with hydrochloric acid;
N-[2-(4-Benzylamino-2-oxo-1,2-dihydro-pyridin-3-yl)-
3H-benzoimidazol-4-yl]-2-methoxy-benzamide; compound with hydrochloric acid;
N-[2-(4-Benzylamino-2-oxo-1,2-dihydro-pyridin-3-yl)-
3H-benzoimidazol-4-yl]-2-chloro-benzamide; compound with hydrochloric acid;
N-[2-(4-Benzylamino-2-oxo-1,2-dihydro-pyridin-3-yl)-
3H-benzoimidazol-4-yl]-4-chloro-benzamide; compound with hydrochloric acid;
N-{2-[4-((S)-2-Hydroxy-2-phenyl-ethylamino)-2-oxo-1,
2-dihydro-pyridin-3-yl]-3H-benzoimidazol-4-yl}-2-
phenyl-acetamide;
N-{2-[4-(3-Chloro-benzylamino)-2-oxo-1,2-dihydro-pyridin-3-yl]-3H-benzoimidazol-4-yl}-benzamide;
N-{2-[4-((S)-2-Hydroxy-2-phenyl-ethylamino)-2-oxo-1,
2-dihydro-pyridin-3-yl]-3H-benzoimidazol-4-yl}-2,2-
dimethyl-propionamide;
N-{2-[4-((S)-2-Hydroxy-2-phenyl-ethylamino)-2-oxo-1,
2-dihydro-pyridin-3-yl]-3H-benzoimidazol-4-yl}-4-
methoxy-benzamide;
N-{2-[4-((S)-2-Hydroxy-2-phenyl-ethylamino)-2-oxo-1,
2-dihydro-pyridin-3-yl]-3H-benzoimidazol-4-yl}-3-
trifluoromethyl-benzamide;
N-{2-[4-((S)-2-Hydroxy-2-phenyl-ethylamino)-2-oxo-1,
2-dihydro-pyridin-3-yl]-3H-benzoimidazol-4-yl}-2-
phenoxy-acetamide;
N-{2-[4-((S)-2-Hydroxy-2-phenyl-ethylamino)-2-oxo-1,
2-dihydro-pyridin-3-yl]-3H-benzoimidazol-4-yl}-3,3-
dimethyl-butyramide;
Cyclopropanecarboxylic acid {2-[4-((S)-2-hydroxy-2-
phenyl-ethylamino)-2-oxo-1,2-dihydro-pyridin-3-yl]-
3H-benzoimidazol-4-yl}-amide;
2-Fluoro-N-{2-[4-((S)-2-hydroxy-2-phenyl-ethylamino)-
2-oxo-1,2-dihydro-pyridin-3-yl]-3H-benzoimidazol-4-
yl}-benzamide;
2-Chloro-N-{2-[4-((S)-2-hydroxy-2-phenyl-ethylamino)-
2-oxo-1,2-dihydro-pyridin-3-yl]-3H-benzoimidazol-4-
yl}-benzamide;
2-(4-Chloro-phenoxy)-N-{2-[4-((S)-2-hydroxy-2-phenyl-ethylamino)-2-oxo-1,2-dihydro-pyridin-3-yl]-3H-
benzoimidazol-4-yl}-acetamide;
3-Cyano-N-{2-[4-((S)-2-hydroxy-2-phenyl-ethylamino)-
2-oxo-1,2-dihydro-pyridin-3-yl]-3H-benzoimidazol-4-
yl}-benzamide;
N-{2-[4-((S)-2-Hydroxy-2-phenyl-ethylamino)-2-oxo-1,
2-dihydro-pyridin-3-yl]-3H-benzoimidazol-4-yl}-2-
methoxy-acetamide;
2,4-Difluoro-N-{2-[4-((S)-2-hydroxy-2-phenyl-ethylamino)-2-oxo-1,2-dihydro-pyridin-3-yl]-3H-benzoimidazol-4-yl}-benzamide;
3-Fluoro-N-{2-[4-((S)-2-hydroxy-2-phenyl-ethylamino)-
2-oxo-1,2-dihydro-pyridin-3-yl]-3H-benzoimidazol-4-
yl}-benzamide;
2,4-Dichloro-N-{2-[4-((S)-2-hydroxy-2-phenyl-ethylamino)-2-oxo-1,2-dihydro-pyridin-3-yl]-3H-benzoimidazol-4-yl}-benzamide;
N-{2-[4-((S)-2-Hydroxy-2-phenyl-ethylamino)-2-oxo-1,
2-dihydro-pyridin-3-yl]-3H-benzoimidazol-4-yl}-3-
methoxy-benzamide;
4-Cyano-N-{2-[4-((S)-2-hydroxy-2-phenyl-ethylamino)-
2-oxo-1,2-dihydro-pyridin-3-yl]-3H-benzoimidazol-4-
yl}-benzamide; and
Furan-2-carboxylic acid {2-[4-((S)-2-hydroxy-2-phenyl-ethylamino)-2-oxo-1,2-dihydro-pyridin-3-yl]-3H-benzoimidazol-4-yl}-amide.

6. A compound according to claim 1 characterized in that $R^1$ is —O—$R^3$.

7. A compound according to claim 6, selected from the group consisting of:
{2-[4-((S)-2-Hydroxy-2-phenyl-ethylamino)-2-oxo-1,2-
dihydro-pyridin-3-yl]-3H-benzoimidazol-4-yl}-carbamic acid 4-methoxy-phenyl ester;
{2-[4-((S)-2-Hydroxy-2-phenyl-ethylamino)-2-oxo-1,2-
dihydro-pyridin-3-yl]-3H-benzoimidazol-4-yl}-carbamic acid 2-methoxy-ethyl ester;
{2-[4-((S)-2-Hydroxy-2-phenyl-ethylamino)-2-oxo-1,2-
dihydro-pyridin-3-yl]-3H-benzoimidazol-4-yl}-carbamic acid 2,2,2-trichloro-1,1-dimethyl-ethyl ester;
{2-[4-((S)-2-Hydroxy-2-phenyl-ethylamino)-2-oxo-1,2-
dihydro-pyridin-3-yl]-3H-benzoimidazol-4-yl}-carbamic acid phenyl ester;
{2-[4-((S)-2-Hydroxy-2-phenyl-ethylamino)-2-oxo-1,2-
dihydro-pyridin-3-yl]-3H-benzoimidazol-4-yl}-carbamic acid allyl ester;
{2-[4-((S)-2-Hydroxy-2-phenyl-ethylamino)-2-oxo-1,2-
dihydro-pyridin-3-yl]-3H-benzoimidazol-4-yl}-carbamic acid isopropyl ester; and
(2-{4-[(S)-2-(3-Chloro-phenyl)-2-hydroxy-ethylamino]-
2-oxo-1,2-dihydro-pyridin-3-yl}-1H-benzoimidazol-4-yl)-carbamic acid methylester.

8. A compound according to claim 1 characterized in that $R^1$ is —NR—$R^3$.

9. A compound according to claim 8, selected from the group consisting of:
1-(3-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea;
1-{2-[4-((S)-2-Hydroxy-2-phenyl-ethylamino)-2-oxo-1,
2-dihydro-pyridin-3-yl]-3H-benzoimidazol-4-yl}-3-(4-
methoxy-phenyl)-urea;
1-(4-Fluoro-phenyl)-3-{2-[4-((S)-2-hydroxy-2-phenyl-ethylamino)-2-oxo-1,2-dihydro-pyridin-3-yl]-3H-benzoimidazol-4-yl}-urea;
1-{2-[4-((S)-2-Hydroxy-2-phenyl-ethylamino)-2-oxo-1,
2-dihydro-pyridin-3-yl]-3H-benzoimidazol-4-yl}-3-(4-
trifluoromethoxy-phenyl)-urea;
1-{2-[4-((S)-2-Hydroxy-2-phenyl-ethylamino)-2-oxo-1,
2-dihydro-pyridin-3-yl]-3H-benzoimidazol-4-yl}-3-
phenyl-urea;
1-{2-[4-((S)-2-Hydroxy-2-phenyl-ethylamino)-2-oxo-1,
2-dihydro-pyridin-3-yl]-3H-benzoimidazol-4-yl}-3-(3-
methoxy-phenyl)-urea;
1-Benzyl-3-{2-[4-((S)-2-hydroxy-2-phenyl-ethylamino)-
2-oxo-1,2-dihydro-pyridin-3-yl]-3H-benzoimidazol-4-
yl]-urea; and
1-(2-Chloro-phenyl)-3-(2-{4-[(S)-2-(3-chloro-phenyl)-2-
hydroxy-ethylamino]-2-oxo-1,2-dihydro-pyridin-3-
yl}-1H-benzoimidazol-4-yl)-urea.

10. A pharmaceutical composition, comprising a compound of claim 1 and a pharmaceutically acceptable carrier.

* * * * *